(12) United States Patent
Sakamoto et al.

(10) Patent No.: US 7,612,217 B2
(45) Date of Patent: Nov. 3, 2009

(54) SULFONIUM COMPOUND

(75) Inventors: Hiromu Sakamoto, Ibaraki (JP); Yukako Harada, Settsu (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/889,352

(22) Filed: Aug. 10, 2007

(65) Prior Publication Data
US 2008/0081925 A1 Apr. 3, 2008

(30) Foreign Application Priority Data

Aug. 18, 2006 (JP) ............... 2006-223039
Nov. 24, 2006 (JP) ............... 2006-316703

(51) Int. Cl.
C07C 309/04 (2006.01)
C07D 327/06 (2006.01)
C07D 333/46 (2006.01)
C07D 335/02 (2006.01)

(52) U.S. Cl. ............... 549/13; 549/14; 549/78; 560/150; 562/109

(58) Field of Classification Search ............... None
See application file for complete search history.

(56) References Cited

U.S. PATENT DOCUMENTS

| | | | |
|---|---|---|---|
| 2,852,554 A * | 9/1958 | England ............... 560/149 |
| 5,624,787 A * | 4/1997 | Watanabe et al. ......... 430/270.1 |
| 6,893,792 B2 | 5/2005 | Miya et al. |
| 7,122,294 B2 * | 10/2006 | Lamanna ............... 430/280.1 |
| 7,304,175 B2 * | 12/2007 | Harada et al. ............... 560/129 |
| 2002/0102491 A1 * | 8/2002 | Kodama et al. ............ 430/270.1 |
| 2003/0194639 A1 * | 10/2003 | Miya et al. ............... 430/270.1 |
| 2006/0160017 A1 | 7/2006 | Takemoto et al. |
| 2007/0078269 A1 * | 4/2007 | Harada et al. ............... 549/266 |
| 2007/0149702 A1 | 6/2007 | Ando et al. |
| 2008/0213695 A1 * | 9/2008 | Yamaguchi et al. ...... 430/281.1 |

FOREIGN PATENT DOCUMENTS

| | | |
|---|---|---|
| JP | 2004-4561 A | 1/2004 |
| JP | 2004-117959 | 4/2004 |

* cited by examiner

*Primary Examiner*—Fiona T Powers
(74) *Attorney, Agent, or Firm*—Birch, Stewart, Kolasch & Birch, LLP

(57) ABSTRACT

The present invention provides a sulfonium compound represented by the formula (I):

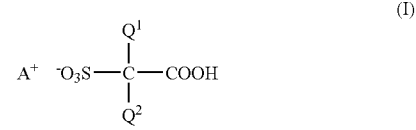

wherein $Q^1$ and $Q^2$ each independently represent a fluorine atom or a C1-C6 perfluoroalkyl group, and $A^+$ represents an organic counter ion.

5 Claims, No Drawings

SULFONIUM COMPOUND

This nonprovisional application claims priority under 35 U.S.C. § 119(a) on Patent Applications No. 2006-223039 filed in JAPAN on Aug. 18, 2006 and No. 2006-316703 filed in JAPAN on Nov. 24, 2006, the entire contents of which are hereby incorporated by reference.

FIELD OF THE INVENTION

The present invention relates to a novel sulfonium compound suitable for a synthetic intermediate of an acid generator used for a chemically amplified resist composition.

BACKGROUND OF THE INVENTION

A chemically amplified positive resist composition used for semiconductor microfabrication employing a lithography process contains an acid generator comprising a compound generating an acid by irradiation.

U.S. 2003/0194639 A1 discloses a chemically amplified resist composition containing the salt represented by the following formula:

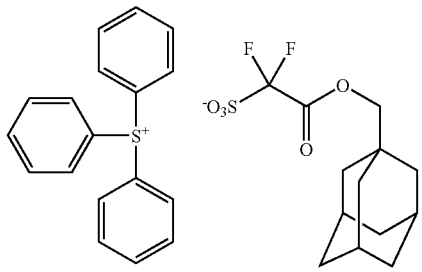

or the like as the acid generator.

There has been demand for development of a compound capable of being derived to the salt having the structure of ester of sulfoacetic acid.

SUMMARY OF THE INVENTION

An object of the present invention is to provide a novel sulfonium compound suitable for a synthetic intermediate of an acid generator capable of providing chemically amplified resist compositions.

Other object of the present invention is to provide a process for producing the same.

Still another object of the present invention is to provide a process for producing a sulfonate compound using the same.

The present invention relates to the followings:

<1> A sulfonium compound represented by the formula (I):

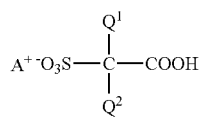

(I)

wherein $Q^1$ and $Q^2$ each independently represent a fluorine atom or a C1-C6 perfluoroalkyl group, and $A^+$ represents an organic counter ion;

<2> The sulfonium compound according to <1>, wherein $Q^1$ and $Q^2$ each independently represent a fluorine atom or a trifluoromethyl group;

<3> The sulfonium compound according to <1> or <2>, wherein the organic counter ion is at least one cation selected from a cation represented by the formula (IIa):

(IIa)

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

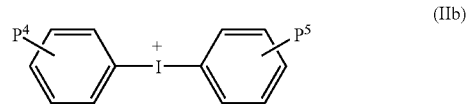

(IIb)

wherein $P^4$ and $P^5$ each independently represent a hydrogen atom, a hydroxyl group, a C1-C12 alkyl group or a C1-C12 alkoxy group, a cation represented by the formula (IIc):

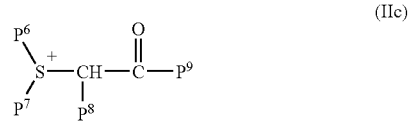

(IIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group may be substituted with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded to form a divalent acyclic hydrocarbon group which forms a 2-oxocycloalkyl group together with the adjacent —CHCO—, and at least one —$CH_2$— in the divalent acyclic hydrocarbon group may be substituted with —CO—, —O— or —S—, and a cation represented by the formula (IId):

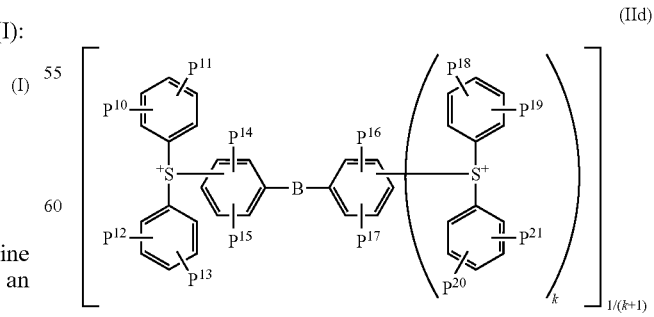

(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1;

<4> The sulfonium compound according to <1> or <2>, wherein the organic counter ion is a cation represented by the formula (IIIa), (IIIb) or (IIIc):

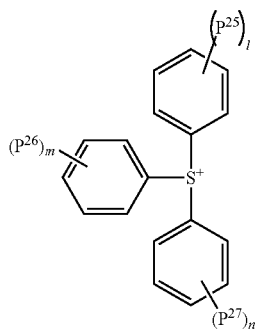
(IIIa)

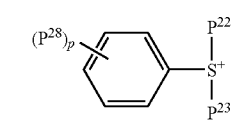
(IIIb)

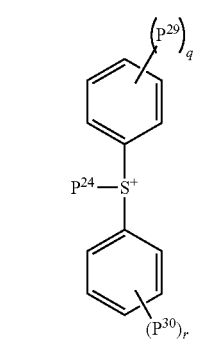
(IIIc)

wherein $P^{22}$, $P^{23}$ and $P^{24}$ each independently represent a C1-C20 alkyl group or a C3-C30 cyclic hydrocarbon group except a phenyl group, wherein at least one hydrogen atom in the C1-C20 alkyl group may be substituted with a hydroxyl group, a C1-C12 alkoxy group or a C3-C12 cyclic hydrocarbon group and wherein at least one hydrogen atom in the C3-C30 cyclic hydrocarbon group may be substituted with a hydroxyl group, a C1-C12 alkyl group or a C1-C12 alkoxy group, and $P^{25}$, $P^{26}$, $P^{27}$, $P^{28}$, $P^{29}$ and $P^{30}$ each independently represent a hydroxyl group, a C1-C12 alkyl group, a C1-C12 alkoxy group or a C3-C12 cyclic hydrocarbon group, and l, m, n, p, q and r each independently represent an integer of 0 to 5;

<5> The sulfonium compound according to <1> or <2>, wherein the organic counter ion is a cation represented by the formula (IIIa):

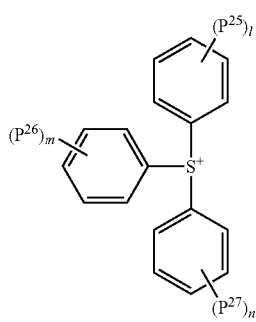
(IIIa)

wherein $P^{25}$, $P^{26}$, $P^{27}$, l, m and n are the same as defined in <4>;

<6> The sulfonium compound according to <1>, wherein the sulfonium compound is one represented by the formula (IV):

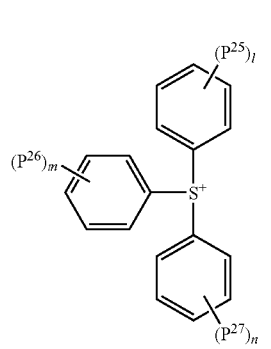
(IV)

wherein $P^{25}$, $P^{26}$, $P^{27}$, l, m and n are the same as defined in <4>;

<7> A process for production of a sulfonium compound represented by the formula (I):

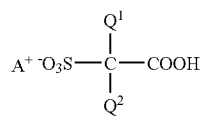
(I)

wherein $Q^1$ and $Q^2$ each independently represent a fluorine atom or a C1-C6 perfluoroalkyl group, and $A^+$ represents an organic counter ion, which comprises reacting a salt represented by the formula (V):

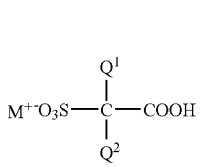
(V)

wherein $Q^1$ and $Q^2$ are the same as defined above, and M represents Li, Na, K or Ag, with a compound represented by the formula (VI):

$$A^+ \ ^-L \qquad (VI)$$

wherein $A^+$ is the same as defined above, and L represents F, Cl, Br, I, $BF_4$, $AsF_6$, $SbF_6$, $PF_6$ or $ClO_4$; and <8> A process for production of a sulfonate compound represented by the formula (VIII):

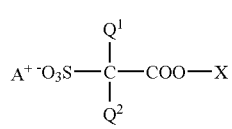
(VIII)

wherein $Q^1$ and $Q^2$ each independently represent a fluorine atom or a C1-C6 perfluoroalkyl group, $A^+$ represents an organic counter ion, and X represents a C1-C30 hydrocarbon group which may be substituted, which comprises reacting a sulfonium compound represented by the formula (I):

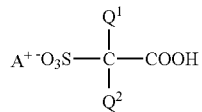
(I)

wherein $Q^1$, $Q^2$ and $A^+$ are the same as defined above, with a compound represented by the formula (VII):

 (VII)

wherein X is the same as defined above.

DESCRIPTION OF PREFERRED EMBODIMENTS

The present invention provides a sulfonium compound represented by the formula (I) (hereinafter, simply referred to as the sulfonium compound (I)).

In the sulfonium compound (I), $Q^1$ and $Q^2$ each independently represent a fluorine atom or a C1-C6 perfluoroalkyl group.

Examples of the C1-C6 perfluoroalkyl group include a trifluoromethyl, pentafluoroethyl, heptafluoropropyl, nonafluorobutyl undecafluoropentyl and tridecafluorohexyl group, and the trifluoromethyl group is preferable.

It is preferred that $Q^1$ and $Q^2$ each independently represent the fluorine atom or the trifluoromethyl group, and it is more preferred that $Q^1$ and $Q^2$ represent the fluorine atoms.

Specific examples of the anion part of the sulfonium compound (I) include the followings:

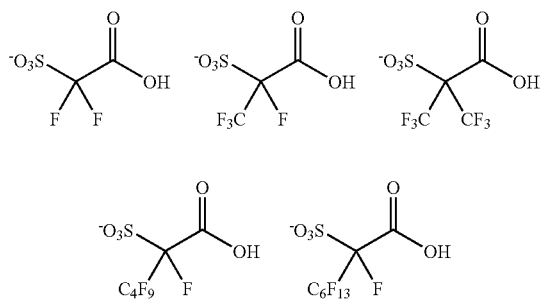

The following anion parts are preferable.

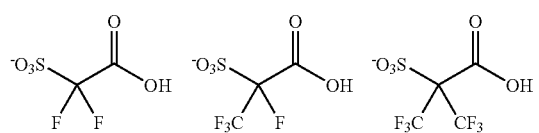

The following anion parts are more preferable.

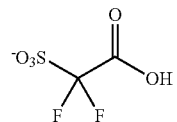

In the formula (I), $A^+$ represents an organic counter ion.

Examples of the organic counter ion include a cation represented by the formula (IIa):

(IIa)

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

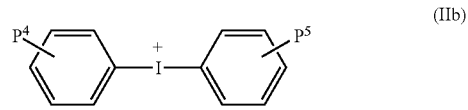
(IIb)

wherein $P^4$ and $P^5$ each independently represent a hydrogen atom, a hydroxyl group, a C1-C12 alkyl group or a C1-C12 alkoxy group, a cation represented by the formula (IIc):

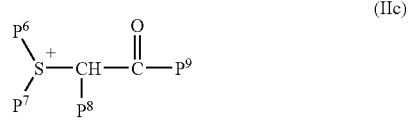
(IIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group may be substituted with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ bond to form a divalent acyclic hydrocarbon group which forms a 2-oxocycloalkyl group together with the adjacent —CHCO—, and at least one —$CH_2$— in the divalent acyclic hydrocarbon group may be substituted with —CO—, —O— or —S—, and a cation represented by the formula (IId):

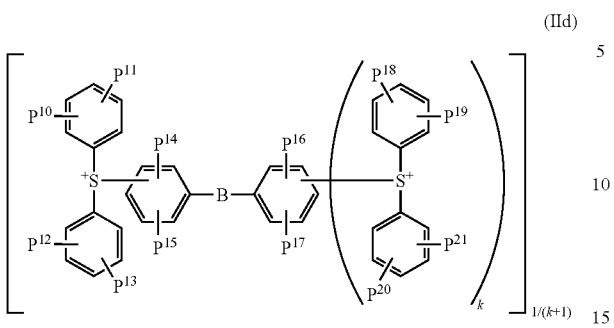

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1.

Examples of the C1-C12 alkoxy group in the formula (IIa) include a methoxy, ethoxy, n-propoxy, isopropoxy, n-butoxy, isobutoxy, sec-butoxy, tert-butoxy, n-pentyloxy, n-hexyloxy, n-octyloxy and 2-ethylhexyloxy group. Examples of the C3-C12 cyclic hydrocarbon group in the formula (IIa) include a cyclopentyl, cyclohexyl, 1-adamantyl, 2-adamantyl, phenyl, 2-methylphenyl, 4-methylphenyl, 1-naphthyl and 2-naphthyl group.

Examples of the C1-C30 alkyl group which may be substituted with at least one selected from the hydroxyl group, the C3-C12 cyclic hydrocarbon group and the C1-C12 alkoxy group in the formula (IIa) include a methyl, ethyl, n-propyl, isopropyl, n-butyl, isobutyl, sec-butyl, tert-butyl, n-pentyl, n-hexyl, n-octyl, 2-ethylhexyl and benzyl group.

Examples of the C3-C30 cyclic hydrocarbon group which may be substituted with at least one selected from the hydroxyl group and the C1-C12 alkoxy group in the formula (IIa) include a cyclopentyl, cyclohexyl, 1-adamantyl, 2-adamantyl, bicyclohexyl, phenyl, 2-methylphenyl, 4-methylphenyl, 4-ethylphenyl, 4-isopropylphenyl, 4-tert-butylphenyl, 2,4-dimethylphenyl, 2,4,6-trimethylphenyl, 4-n-hexylphenyl, 4-n-octylphenyl, 1-naphthyl, 2-naphthyl, fluorenyl, 4-phenylphenyl, 4-hydroxyphenyl, 4-methoxyphenyl, 4-tert-butoxyphenyl, 4-n-hexyloxyphenyl group.

Examples of the C1-C12 alkyl group in the formulae (IIb), (IIc) and (IId) include a methyl, ethyl, n-propyl, isopropyl, n-butyl, isobutyl, sec-butyl, tert-butyl, n-pentyl, n-hexyl, n-octyl and 2-ethylhexyl group. Examples of the C1-C12 alkoxy group in the formulae (IIb) and (IId) include the same groups as mentioned in the above formula (IIa).

Examples of the C3-C12 cycloalkyl group in the formula (IIc) include a cyclopropyl, cyclobutyl, cyclopentyl, cyclohexyl, cycloheptyl, cycooctyl and cyclodecyl group. Examples of the C3-C12 divalent acyclic hydrocarbon group formed by bonding $P^6$ and $P^7$ include a trimethylene, tetramethylene, pentamethylene group. Examples of the ring group formed together with the adjacent $S^+$ and the divalent acyclic hydrocarbon group include a tetramethylenesulfonio, pentamethylenesulfonio and oxybisethylenesulfonio group.

Examples of the aromatic group in the formula (IIc) include a phenyl, tolyl, xylyl and naphthyl group. Examples of the divalent acyclic hydrocarbon group formed by bonding $P^8$ and $P^9$ include a methylene, ethylene, trimethylene, tetramethylene and pentamethylene group and examples of the 2-oxocycloalkyl group formed together with the adjacent —CHCO— and the divalent acyclic hydrocarbon group include a 2-oxocyclopentyl and 2-oxocyclohexyl group.

The cation represented by the formula (IIa) or (IIc) is preferable and the cation represented by the formula (IIa) is more preferable.

In the cation represented by the formula (IIa), cations represented by the following formulae (IIIa), (IIIb) and (IIIc) are preferable, and the cation represented by the formula (IIIa) is more preferable.

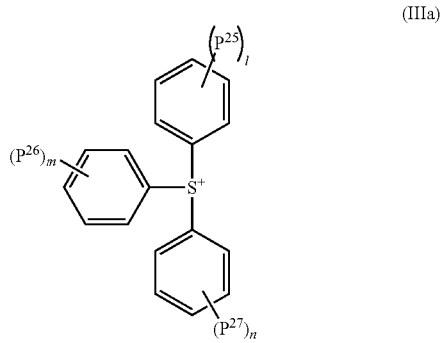

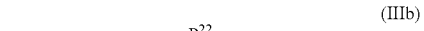

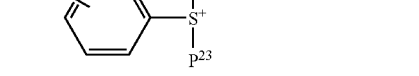

$P^{22}$, $P^{23}$ and $P^{24}$ each independently represent a C1-C20 alkyl group or a C3-C30 cyclic hydrocarbon group except a phenyl group. At least one hydrogen atom in the C1-C20 alkyl group in the formulae (IIIa), (IIIb) and (IIIc) may be substituted with a hydroxyl group, a C1-C12 alkoxy group or a C3-C12 cyclic hydrocarbon group. At least one hydrogen atom in the C3-C30 cyclic hydrocarbon group may be substituted with a hydroxyl group, a C1-C12 alkyl group or a C1-C12 alkoxy group. Examples of the alkyl group, the alkoxy group and the cyclic hydrocarbon group include the same groups as mentioned above.

$P^{25}$, $P^{26}$, $P^{27}$, $P^{28}$, $P^{29}$ and $P^{30}$ each independently represent a hydroxyl group, a C1-C12 alkyl group, a C1-C12 alkoxy group or a C3-C12 cyclic hydrocarbon group, and l, m, n, p, q and r each independently represent an integer of 0 to 5. Examples of the alkyl group, the alkoxy group and the cyclic hydrocarbon group include the same groups as mentioned above.

Examples of the cation represented by the formula (IIa) include the followings.

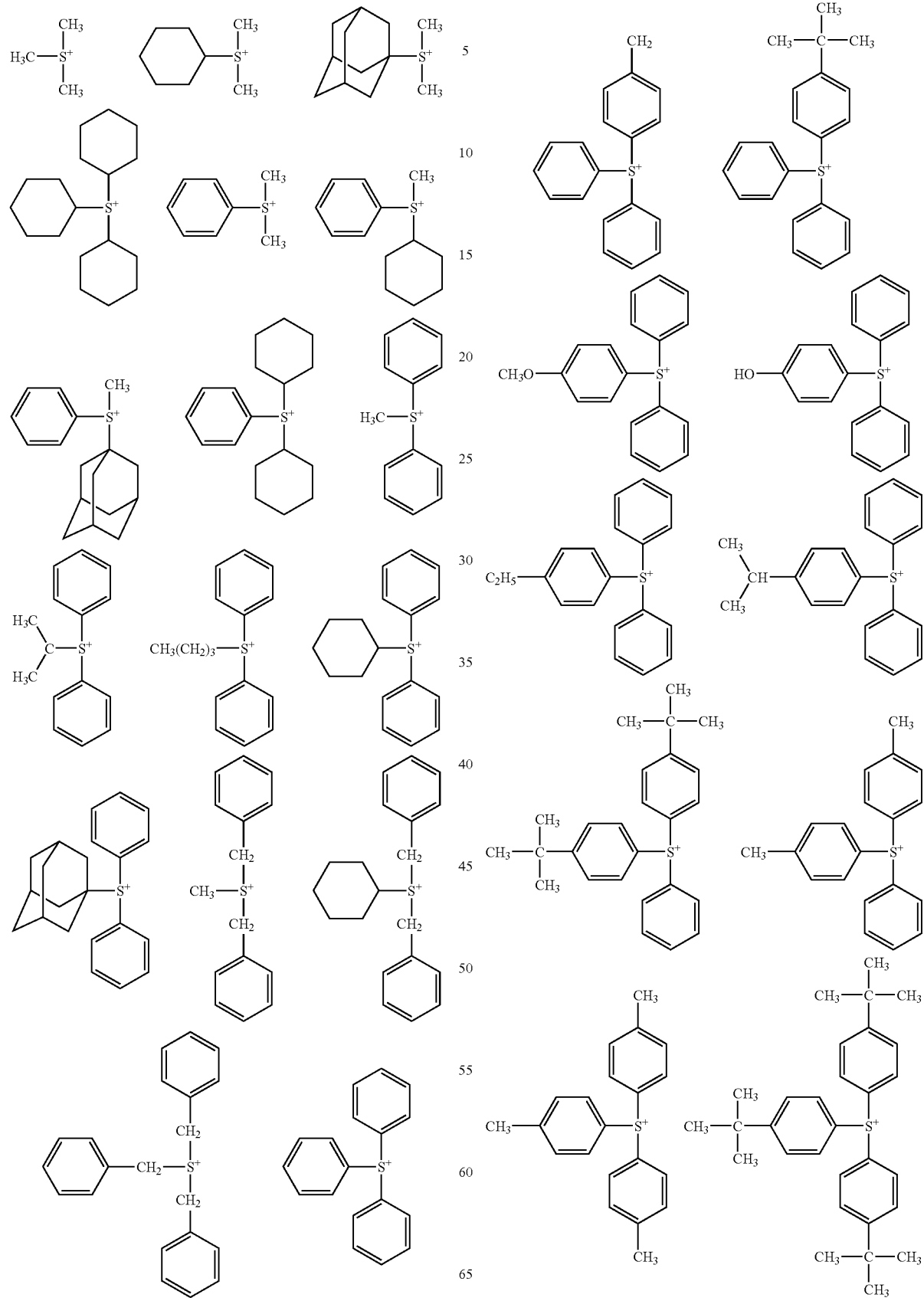

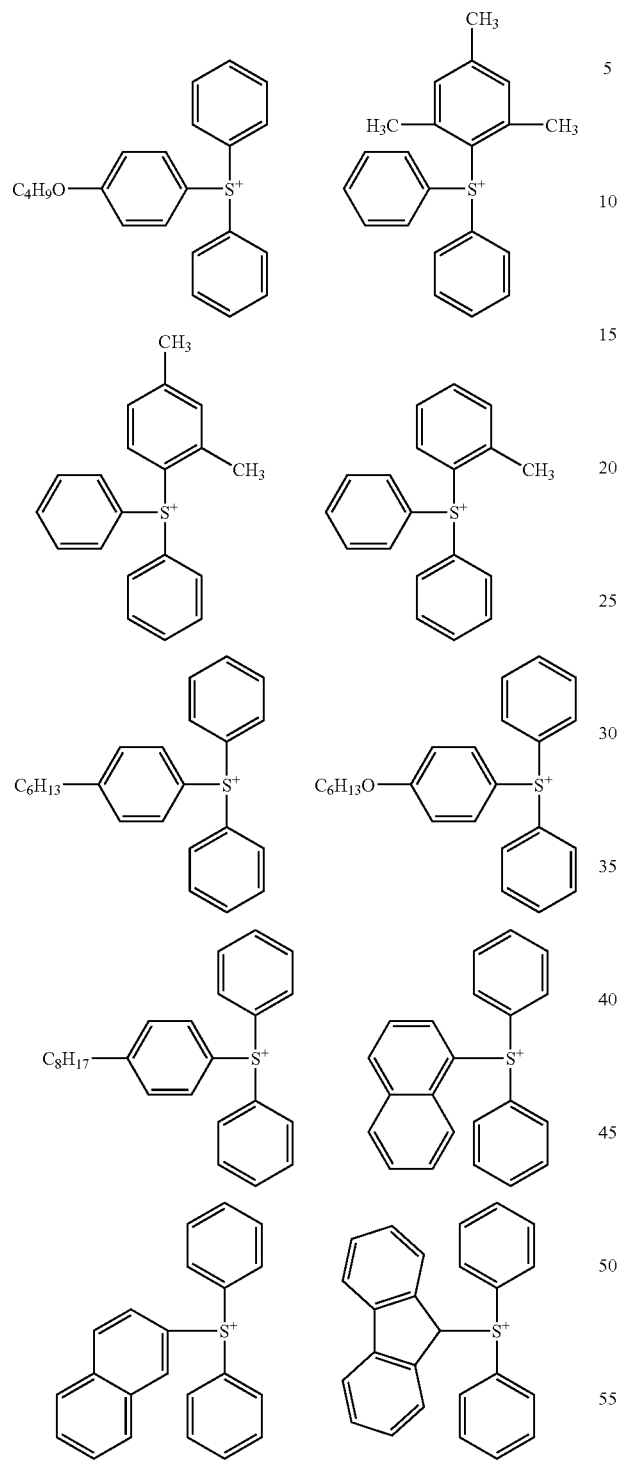
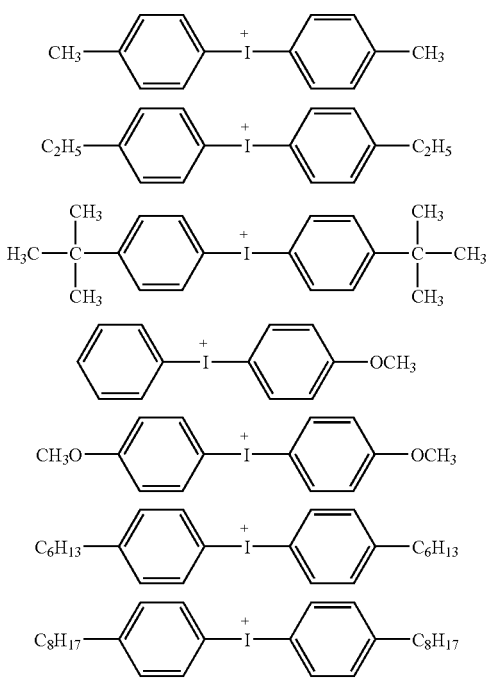
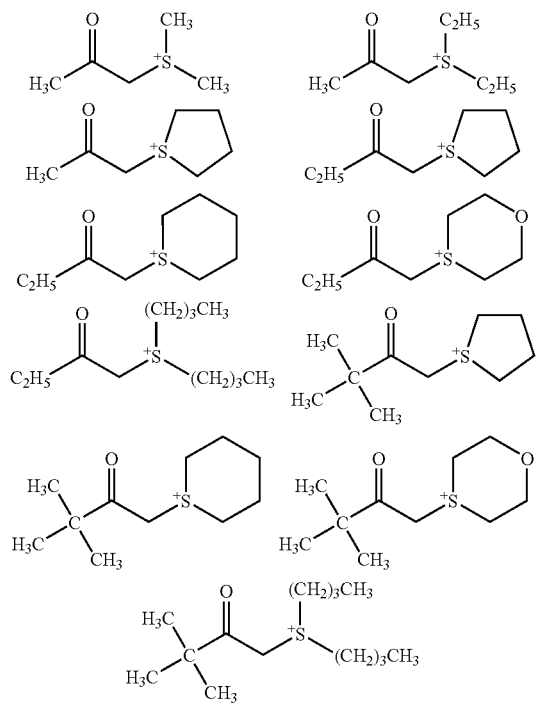
Examples of the cation represented by the formula (IIb) include the followings.
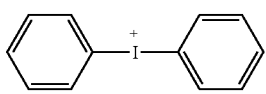
Examples of the cation represented by the formula (IIc) include the followings.
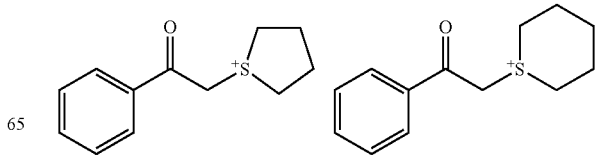

-continued

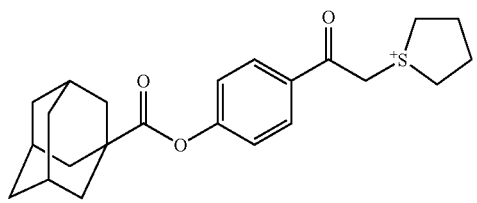
Examples of the cation represented by the formula (IId) include the followings.
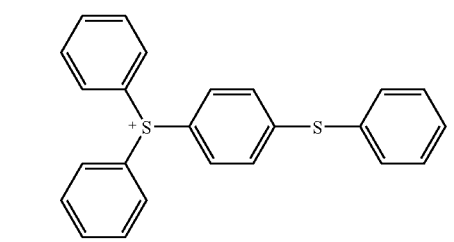
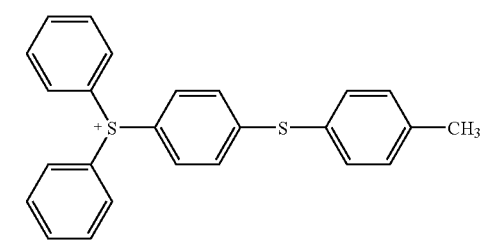
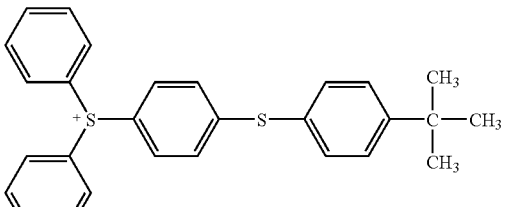
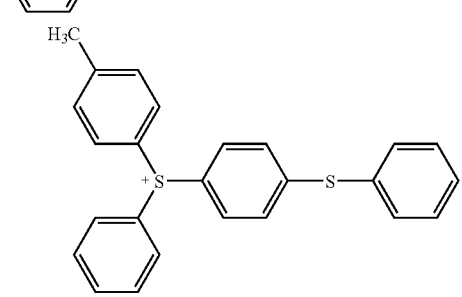
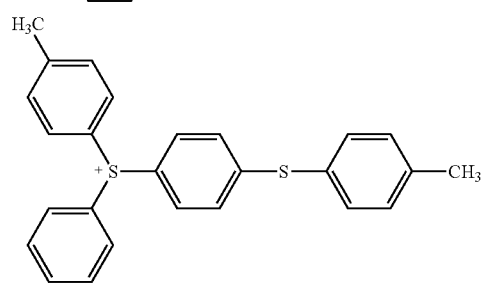
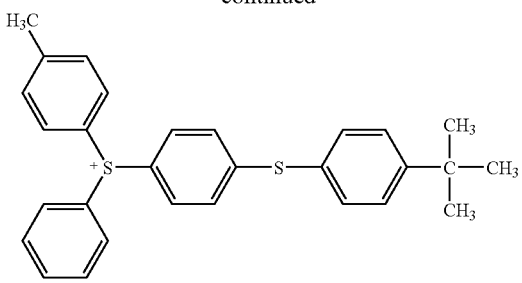
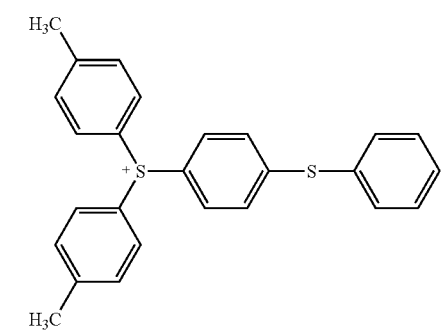
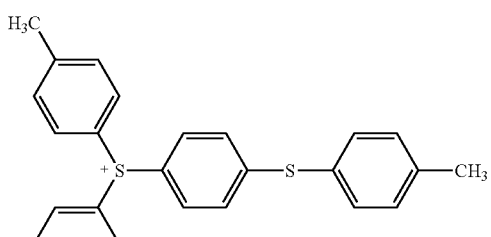
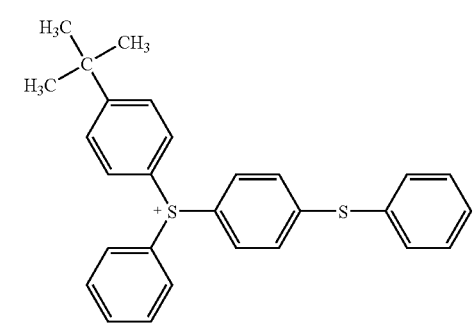
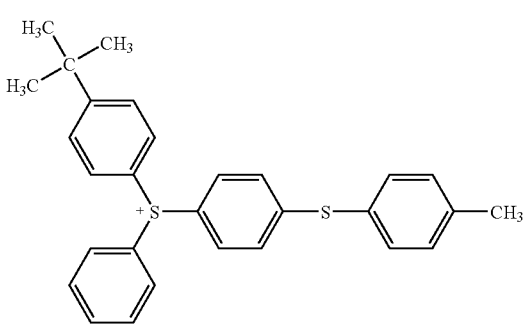

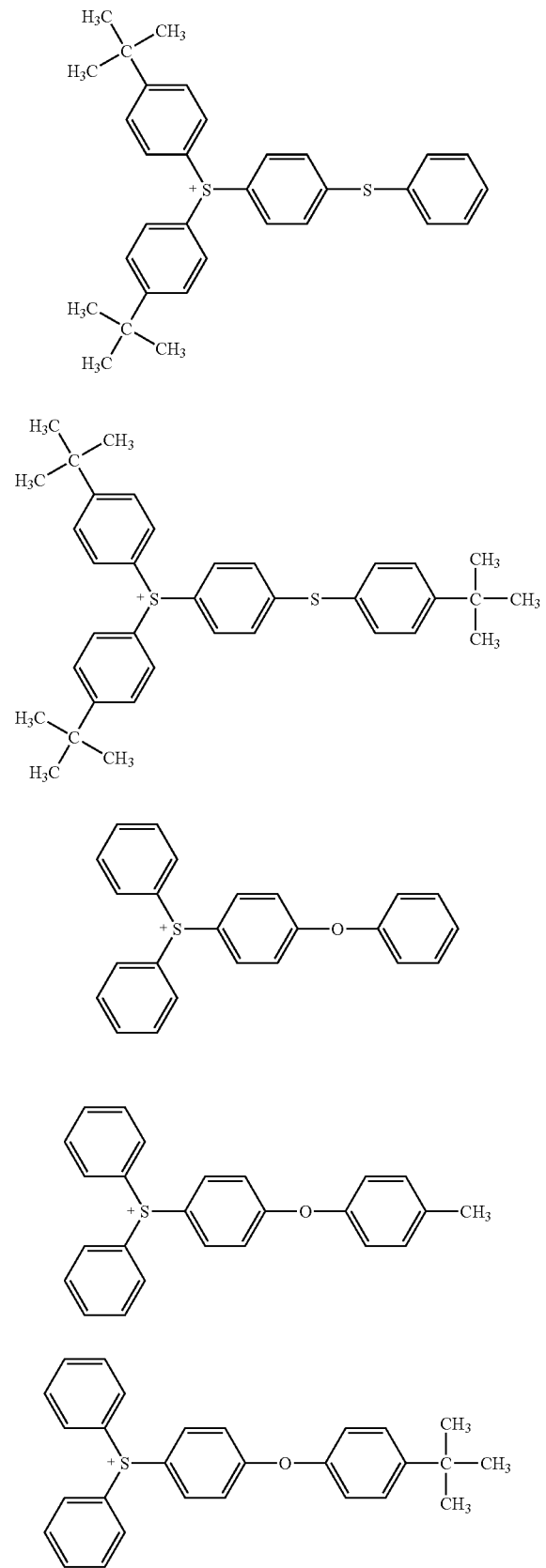
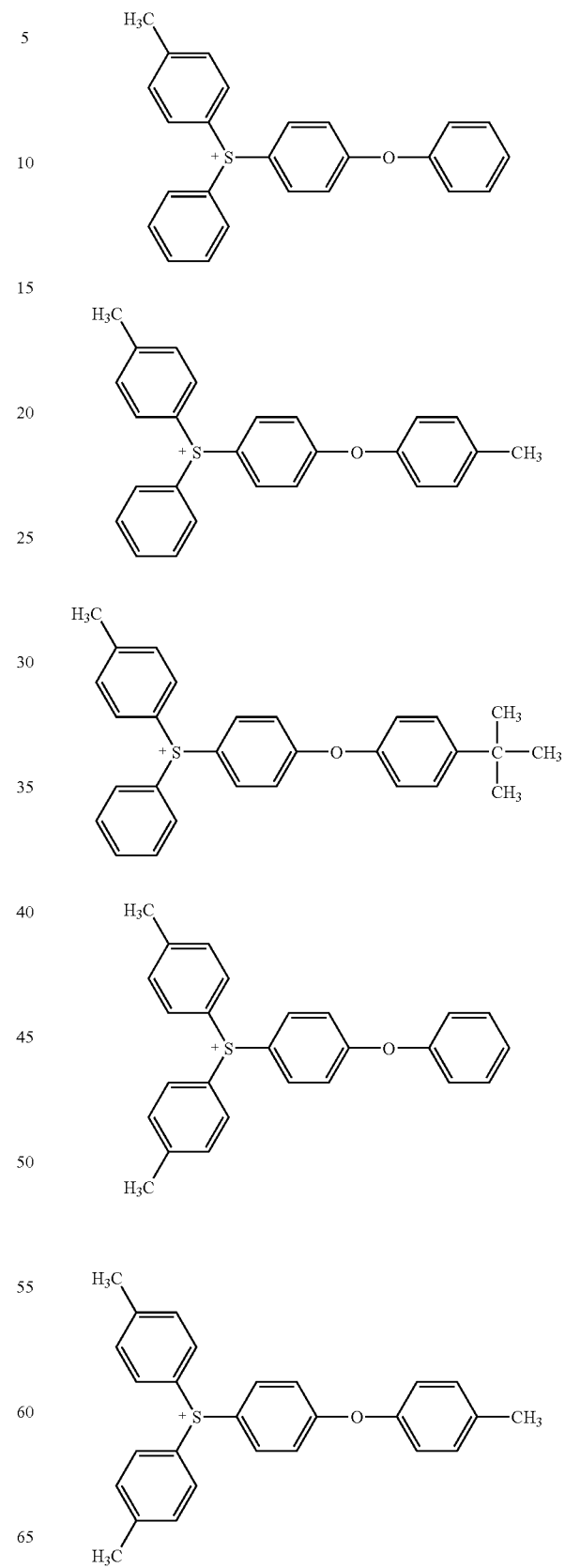

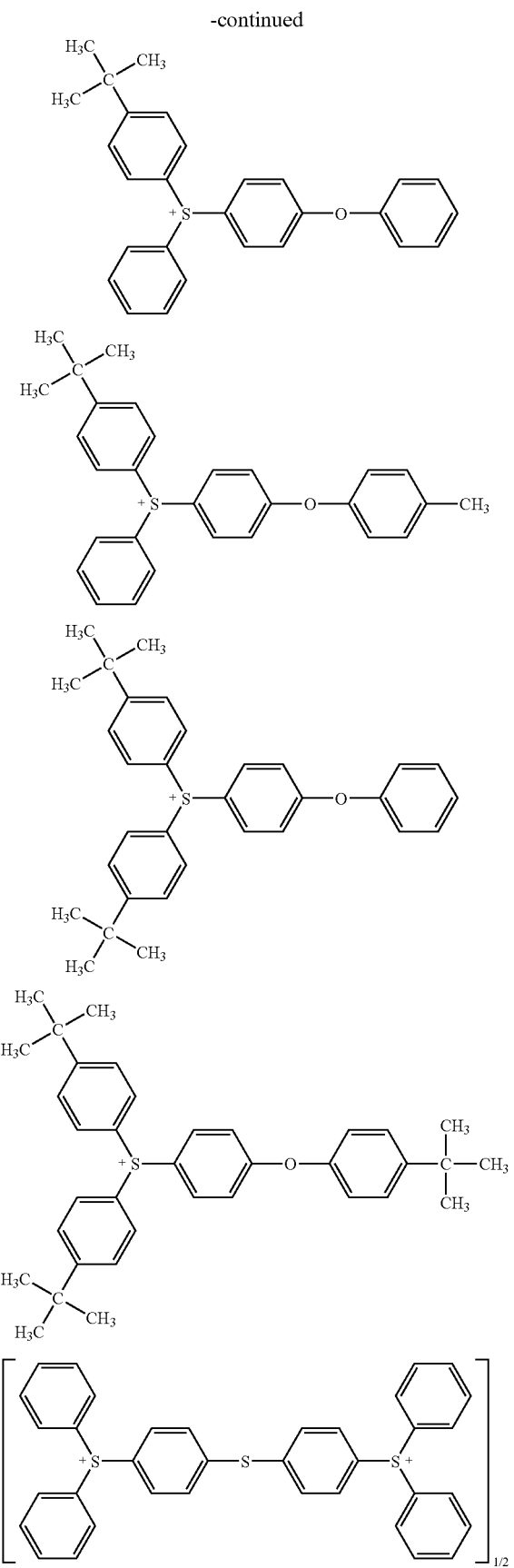
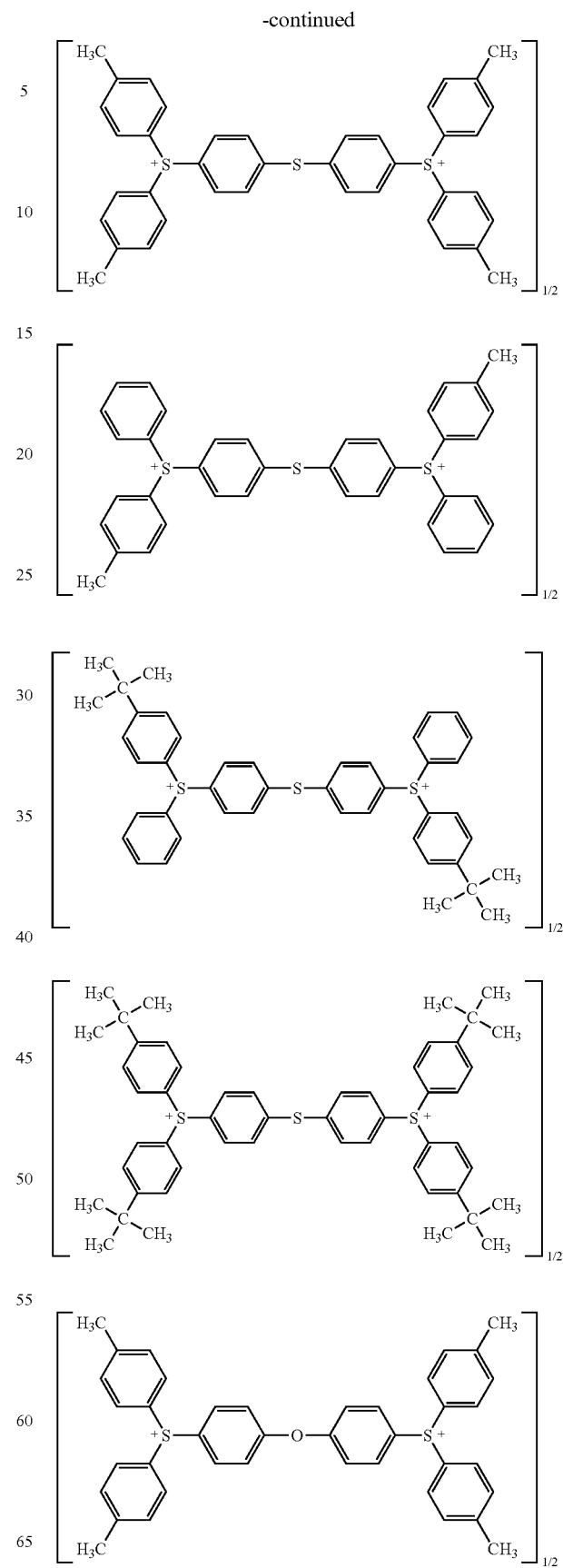

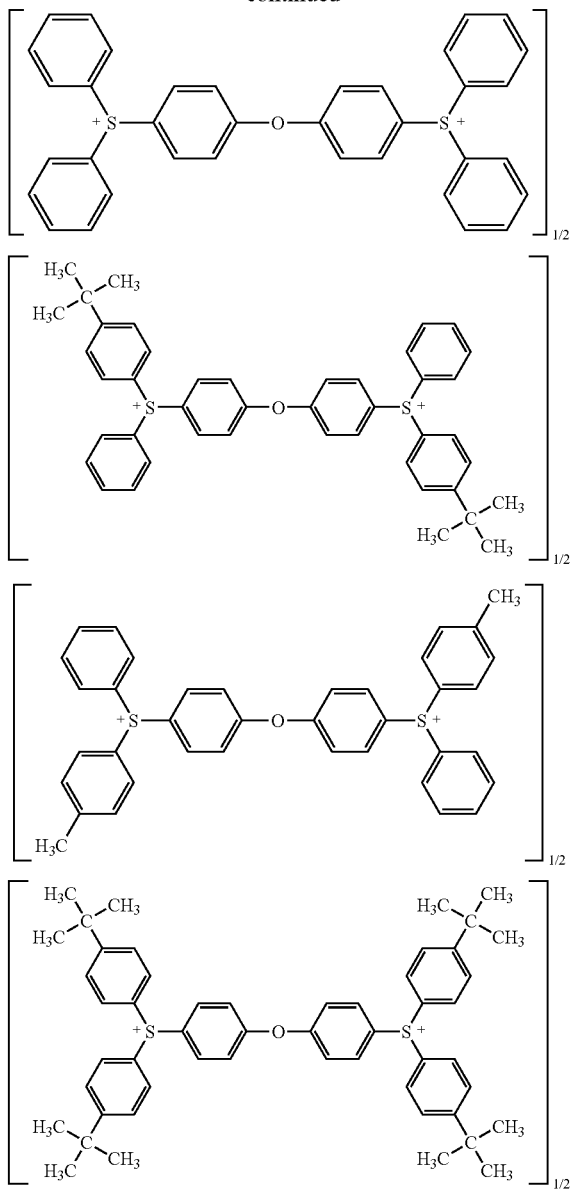

As the sulfonium compound (I), the sulfonium compound represented by the formula (IV):

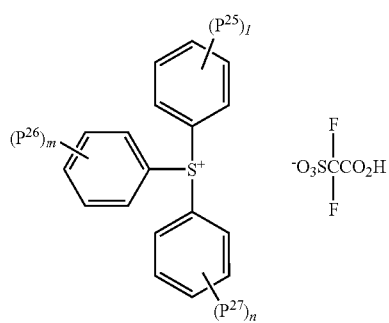

wherein $P^{25}$, $P^{26}$, $P^{27}$, l, m and n are the same as defined above, is preferred.

The sulfonium compound (I) can be produced by a process comprising reacting a salt represented by the formula (V):

wherein $Q^1$ and $Q^2$ are the same as defined above, and M represents Li, Na, K or Ag (hereinafter, simply referred to as the salt (V)), with a compound represented by the formula (VI):

$$A^+{}^-L \qquad (VI)$$

wherein $A^+$ is the same as defined above and L represents F, Cl, Br, I, $BF_4$, $AsF_6$, $SbF_6$, $PF_6$ or $ClO_4$ (hereinafter, simply referred to as the compound (VI)). The reaction of the salt (V) and the compound (VI) is usually conducted in an inert solvent such as water, acetonitrile, chloroform and dichloromethane, at a temperature of 0 to 100° C., preferably of 0 to 60° C.

As the compound (VI), commercially available one is usually used.

The amount of the compound (VI) to be used is usually 0.5 to 2 moles relative to 1 mole of the salt (V). The sulfonium compound (I) obtained may be taken out by crystallization or washing with water.

A sulfonate compound represented by the formula (VIII):

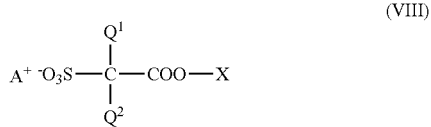

wherein $Q^1$, $Q^2$ and $A^+$ are the same as defined above, and X represents a C1-C30 hydrocarbon group which may be substituted (hereinafter, simply referred to as the sulfonate compound (VIII)), can be produced by a process which comprises reacting the sulfonium compound thus obtained with a compound represented by the formula (VII):

$$HO-X \qquad (VII)$$

wherein X is the same as defined above (hereinafter, simply referred to as the compound (VII)).

The C1-C30 hydrocarbon group may be substituted with at least one substituent. The C1-C30 hydrocarbon group may be linear or branched chain hydrocarbon group. The C1-C30 hydrocarbon group may be monocyclic or polycyclic hydrocarbon group. The C1-C30 hydrocarbon group may have at least one selected from a double bond and an aromatic group. At least one $—CH_2—$ in the C1-C30 hydrocarbon group may be substituted with $—O—$ or $—CO—$.

Examples of the C1-C30 hydrocarbon group include a C1-C30 alkyl group such as a methyl, ethyl, n-propyl, isopropyl, n-butyl, tert-butyl, n-hexyl, n-heptyl, n-octyl, n-decyl, n-undecyl and icosyl group; a C3-C30 cycloalkyl group such as a cyclopentyl, 1-methylcyclopentyl, 1-ethylcyclopentyl, cyclohexyl, 1-methylcyclohexyl, 1-ethylcyclohexyl, 1-n- propylcyclohexyl, norbornyl, 2-methylnorbornyl, 2-ethylnorbornyl, adamantly, 2-methyladamantyl, 2-ethyladamantyl group; a C4-C30 cycloalkyl-substituted alkyl group such as a cyclohexylmethyl, 2-norbornylmethyl and 1-adamantylmethyl group; a C6-C30 aryl group such as a phenyl, naphthyl, fluorenyl, anthryl and phenanthryl group; and a C7-C30 aralkyl group such as a benzyl, (2-naphthyl)methyl, 2-(2-naphthyl)ethyl, 2-(1-naphthyl)ethyl, 3-(1-naphthyl)propyl, (9-fluorenyl)methyl, (9-anthryl)methyl and (9-phenanthryl)methyl group.

Examples of the substituent include a hydroxyl group; a cyano group; a C1-C6 alkoxy group such as a methoxy, ethoxy, n-propoxy, isopropoxy, n-butoxy, isobutoxy, tert-butoxy, n-pentyloxy and n-hexyloxy group; a C1-C4 perfluoroalkyl group such as a trifluoromethyl, pentafluoroethyl, heptafluoropropyl and nonafluorobutyl group; a C1-C6 hydroxyalkyl group such as a hydroxymethyl, 2-hydroxyethyl, 3-hydroxypropyl, 4-hydroxybutyl and 6-hydroxyhexyl group.

Specific examples of C1-C30 hydrocarbon group which may be substituted include the followings.

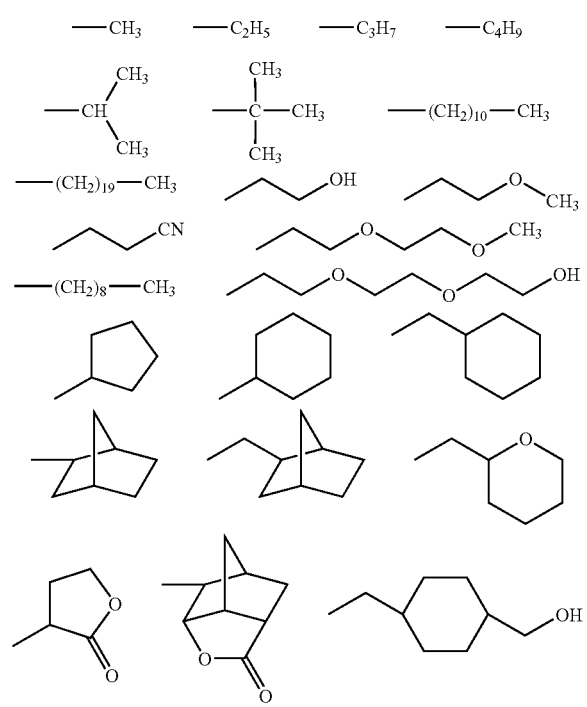

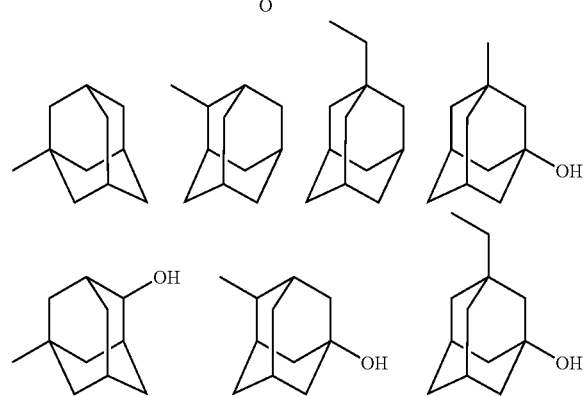

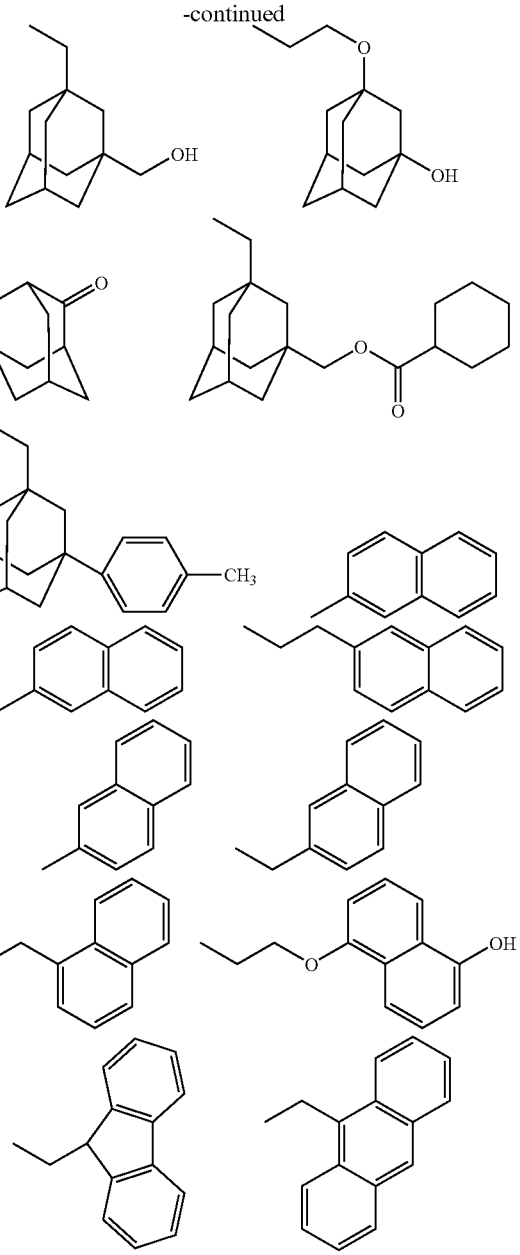

In the above formulae, the straight line with an open end shows a bond extended from an adjacent group.

Specific examples of the compound (VII) include the followings.

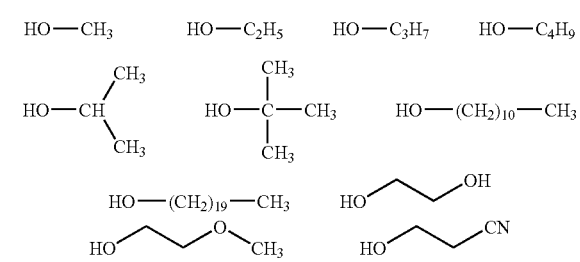

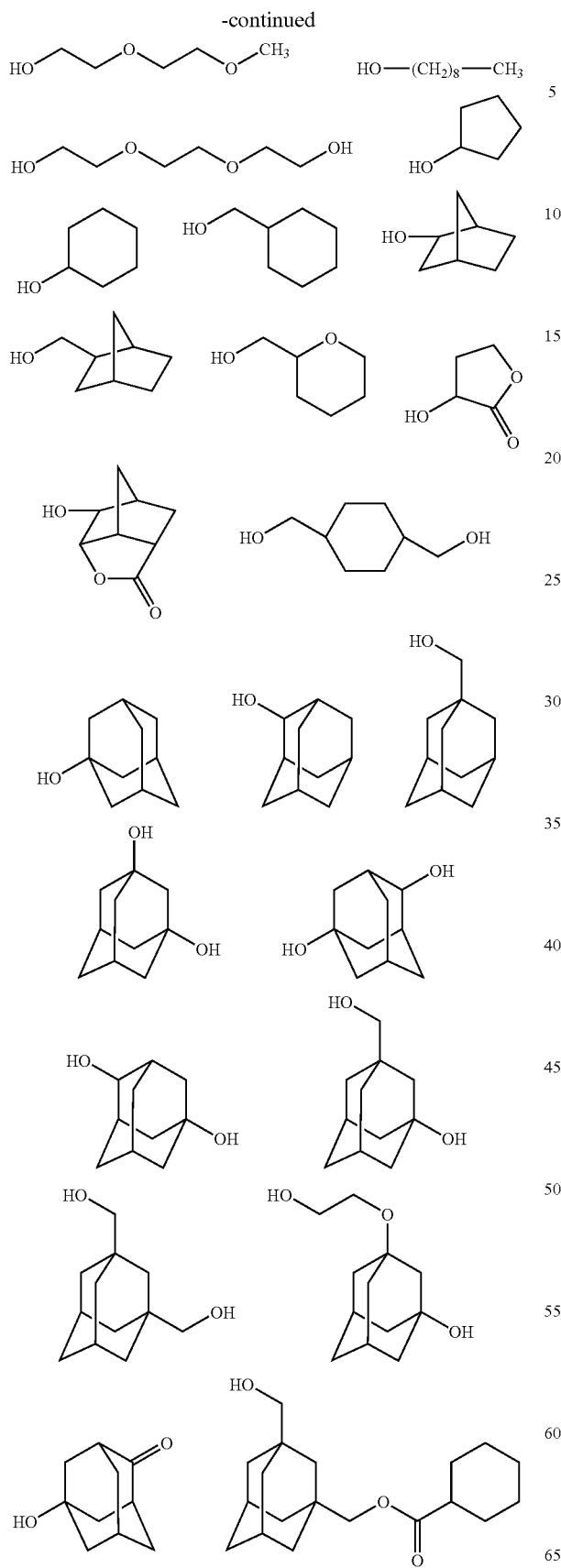

As the compound (VII), commercially available one is usually used.

The reaction of the sulfonium compound (I) and the compound (VII) is usually conducted by mixing them in an aprotic solvent such as chloroform, dichloromethane, dichloroethane, toluene, xylene, ethylbenzene, monochlorobenzene, acetonitrile and N,N-dimethylformamide, at a temperature of 20 to 200° C., preferably 50 to 150° C. The reaction can be usually carried out in the presence of an acid or a dehydrating agent. Examples of the acid include an organic acid such as p-toluenesulfonic acid and an inorganic acid such as sulfuric acid. Examples of the dehydrating agent include 1,1'-carbonyldiimidazole and N,N'-dicyclohexylcarbodiimide.

The reaction of the sulfonium compound (I) and the compound (VII) in the presence of the acid may also preferably be conducted while removing water generated, for example, by Dean Stark method as the reaction time tends to be shortened. The reaction may be conducted in the presence of molecular sieves or calcium chloride as the dehydrating agent.

The amount of the sulfonium compound (I) to be used is usually 0.2 to 3 moles, preferably 0.5 to 2 moles relative to 1 mole of the compound (VII). The amount of the acid to be used may be catalytic amount or the amount equivalent to solvent, and it is usually 0.001 to 5 moles relative to 1 mole of the compound (VII). The amount of the dehydrating agent to be used is usually 0.2 to 5 moles, preferably 0.5 to 3 moles relative to 1 mole of the compound (VII).

The sulfonate compound (VIII) obtained may be isolated from the reaction mixture by extraction and concentration of the organic layer obtained.

Examples of the sulfonate compound (VIII) include the followings:

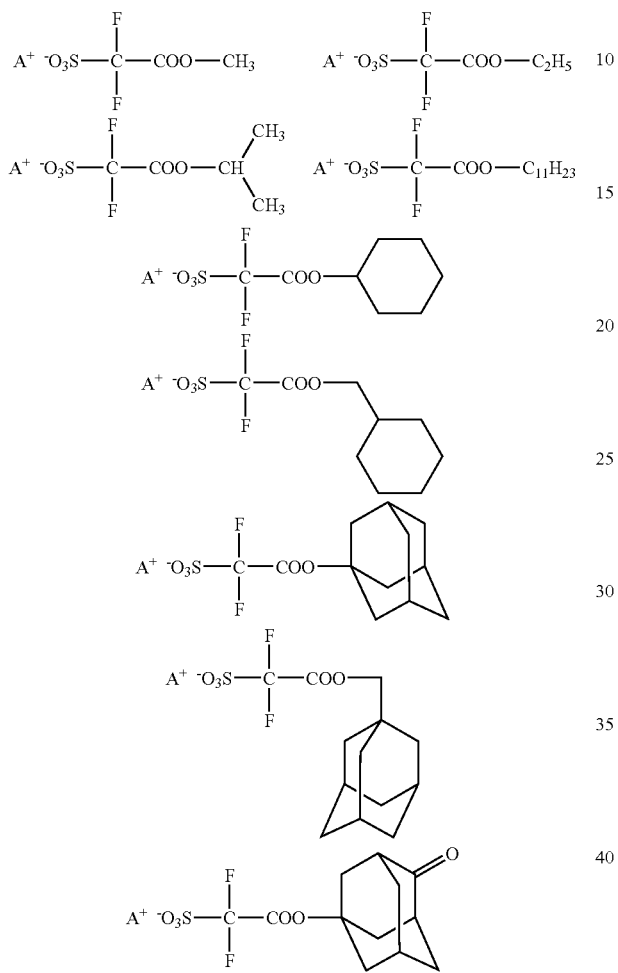

wherein $A^+$ are the same as defined above.

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be described more specifically by Examples, which are not construed to limit the scope of the present invention. The "%" and "part(s)" used to represent the content of any compound and the amount of any material to be used in the following Examples are on a weight basis unless otherwise specifically noted. Structures of compounds obtained were determined by NMR (EX-270 Type manufactured by JEOL LTD.) and mass spectrometry (Liquid Chromatography: 1100 Type manufactured by AGILENT TECHNOLOGIES LTD., Mass Spectrometry: LC/MSD Type or LC/MSD TOF Type manufactured by AGILENT TECHNOLOGIES LTD.).

EXAMPLE 1

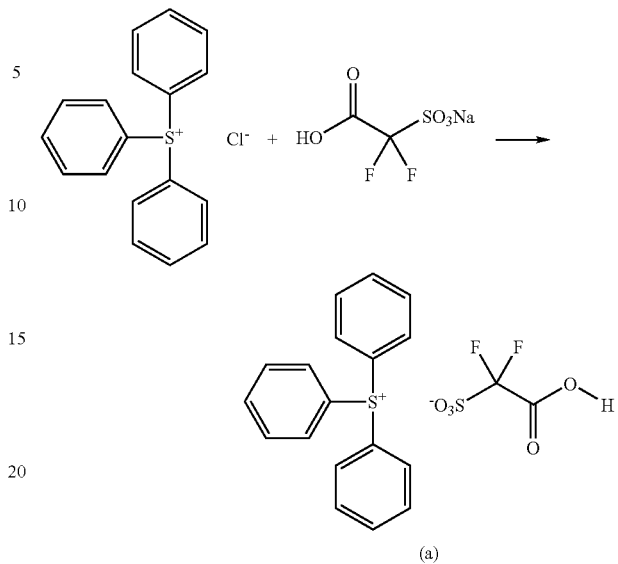

(a)

300.0 Parts of 18% aqueous sodium salt of difluorosulfoacetic acid solution was added to 573.7 parts of 14.2% aqueous triphenylsulfonium chloride solution and the resultant mixture was stirred at 25° C. for about 20 hours. The white precipitates were filtrated, washed with 100 parts of ion-exchanged water and then dried to obtain 88.4 parts of the sulfonium compound represented by the above-mentioned formula (a).

1H-NMR (dimethylsulfoxide-$d_6$, Internal standard: tetramethylsilane): δ (ppm) 7.77-7.88 (m, 15H), 13.90 (br, 1H) MS (ESI(+) Spectrum): $M^+$ 263.2 ($C_{18}H_{15}S^+$=263.09) MS (ESI(−) Spectrum): $M^-$ 175.0 ($C_2HF_2O_5S^-$=174.95)

EXAMPLE 2

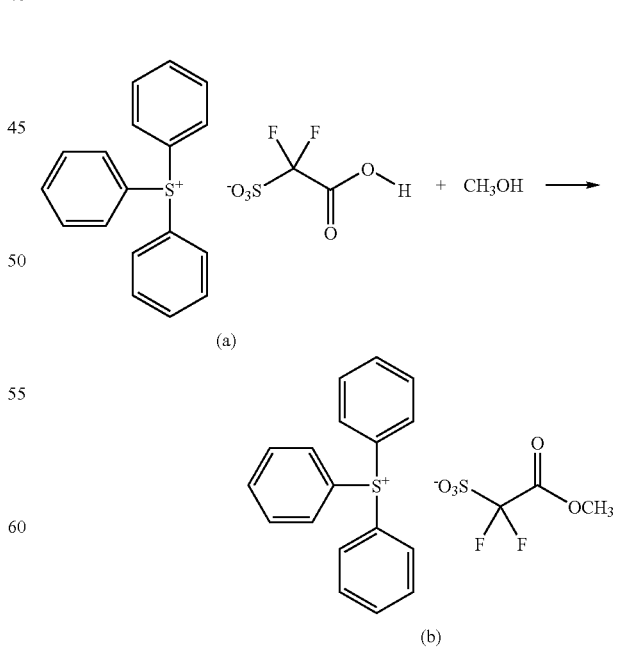

To a reaction container equipped with a packed tower containing molecular sieves 3A for dehydration of reflux liquid, 250.0 parts of the sulfonium compound represented by the above-mentioned formula (a) and 750.0 parts of methanol were added. To the solution obtained, 5.56 parts of sulfuric acid was added and the resultant mixture was refluxed for 12 hours. The reaction mixture was concentrated to remove methanol and 854.4 parts of chloroform and 213.6 parts of ion-exchanged water were added to the residue. The resultant mixture was stirred and allowed to stand to separate into an organic layer and an aqueous layer. The organic layer was repeated to wash with 213.6 parts of ion-exchanged water until the aqueous layer obtained was neutralized. The organic layer obtained was filtrated and concentrated to obtain the residue. 160.8 Parts of acetonitrile was added to the residue and the resultant mixture was concentrated. To the residue obtained, 655.6 parts of tert-butyl methyl ether was added. The resultant mixture was stirred to precipitate the white solid. The white solid precipitated was filtrated and dried to obtain 225.0 parts of the sulfonate compound represented by the above-mentioned formula (b).

$^1$H-NMR (dimethylsulfoxide-$d_6$, Internal standard: tetramethylsilane): δ (ppm) 3.76 (s, 3H), 7.75-7.90 (m, 15H)

EXAMPLE 3

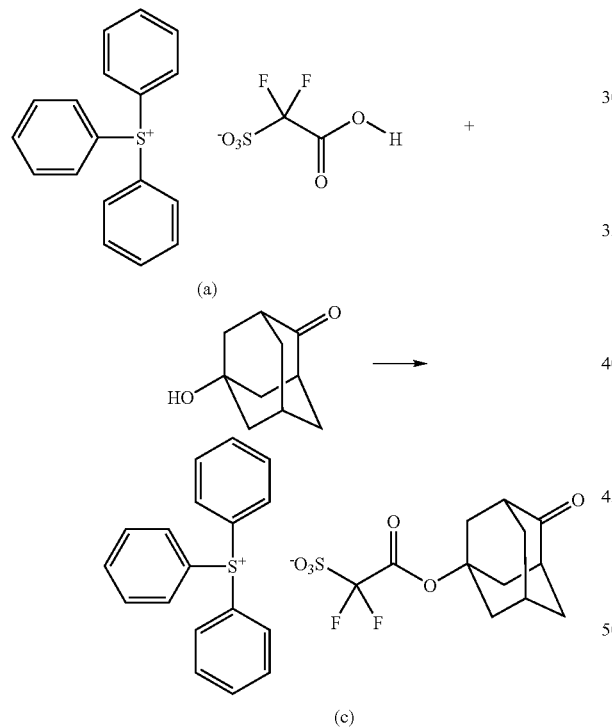

To a reaction container equipped with a packed tower containing molecular sieves 3A for dehydration of reflux liquid, 18.3 parts of the sulfonium compound represented by the above-mentioned formula (a), 6.9 parts of 5-hydroxy-2-adamantanone and 120.0 parts of monochlorobenzene were added. 0.8 Parts of sulfuric acid was added to the mixture obtained and the resultant mixture was refluxed for 15 hours. The reaction mixture was cooled and 100.0 parts of chloroform and 50 parts of ion-exchanged water were added thereto. The resultant mixture was stirred and allowed to stand to separate into an organic layer and an aqueous layer. The organic layer was repeated to wash with 50 parts of ion-exchanged water until the aqueous layer obtained was neutralized. The organic layer obtained was concentrated to obtain the residue. 60 Parts of acetonitrile was added to the residue and the resultant mixture was concentrated. 170 Parts of ethyl acetate was added to the residue obtained. The resultant mixture was stirred to precipitate the white solid. The white solid precipitated was filtrated, washed with 20 parts of ethyl acetate and then dried to obtain 17.8 parts of the sulfonate compound represented by the above-mentioned formula (c).

$^1$H-NMR (dimethylsulfoxide-$d_6$, Internal standard: tetramethylsilane): δ (ppm) 1.83 (d, 2H, J=12.7 Hz), 2.00 (d, 2H, J=12.0 Hz), 2.29-2.32 (m, 7H), 2.53 (s, 2H), 7.75-7.91 (m, 15H) MS (ESI(+) Spectrum): M$^+$ 263.2 ($C_{18}H_{15}S^+$=263.09) MS (ESI(−) Spectrum): M$^−$ 323.0 ($C_{12}H_{13}F_2O_6S^−$=323.04)

EXAMPLE 4

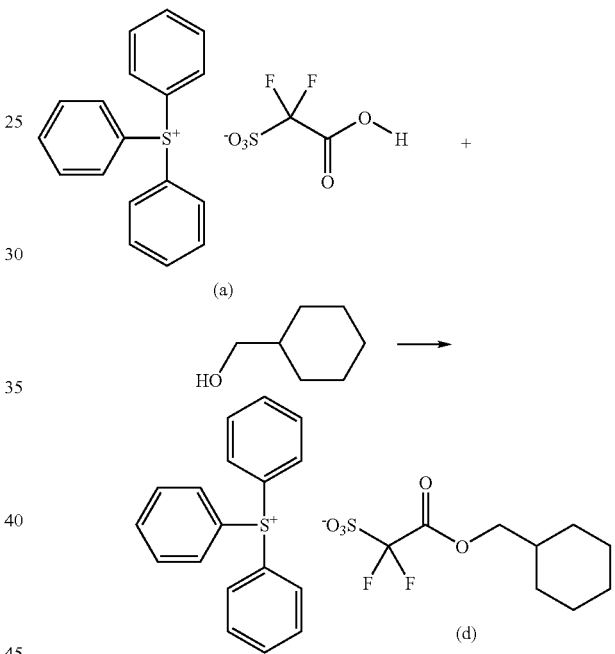

13.0 Parts of p-toluenesulfonic acid was added to a mixture of 298.6 parts of the sulfonium compound represented by the above-mentioned formula (a), 77.8 parts of cyclohexylmethanol and 1194 parts of monochlorobenzene, and the resultant mixture was refluxed for 12 hours.

The reaction mixture was cooled and concentrated to remove monochlorobenzene. 1375 Parts of chloroform was added to the residue obtained and the resultant solution was repeated to wash with 412 parts of ion-exchanged water until the aqueous layer obtained was neutralized.

The organic layer obtained was concentrated and 375 parts of acetonitrile was added to the residue obtained. The mixture obtained was concentrated and 2185 parts of tert-butyl methyl ether was added to the residue obtained. The mixture obtained was stirred and the white solid precipitated was filtrated to obtain 325.4 parts of the sulfonate compound represented by the above-mentioned formula (d).

1H-NMR (dimethylsulfoxide-$d_6$, Internal standard: tetramethylsilane): δ (ppm) 0.88-1.28 (m, 5H), 1.56-1.71 (m, 6H), 4.01 (d, 2H), 7.75-7.90 (m, 15H) MS (ESI(+) Spectrum):

$M^+$ 263.1 ($C_{18}H_{15}S^+$=263.09) MS (ESI(−)) Spectrum): $M^-$ 271.1 ($C_9H_{13}F_2O_5S^-$=271.05)

The sulfonium compound represented by the formula (I) is suitably used for a synthetic intermediate for an acid generator capable of providing chemically amplified positive resist compositions.

What is claimed is:

1. A sulfonium compound represented by the formula (I):

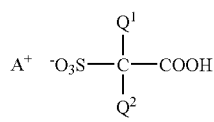
(I)

wherein $Q^1$ and $Q^2$ each independently represent a fluorine atom or a C1-C6 perfluoroalkyl group, and $A^+$ represents an organic counter ion;

wherein the organic counter ion is at least one cation selected from a cation represented by the formula (IIa):

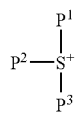
(IIa)

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

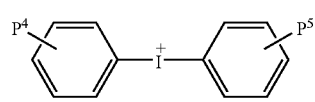
(IIb)

wherein $P^4$ and $P^5$ each independently represent a hydrogen atom, a hydroxyl group, a C1-C12 alkyl group or a C1-C12 alkoxy group, a cation represented by the formula (IIc):

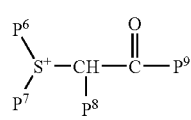
(IIc)

wherein $P^6$ and $P^7$ each independently represent a C1-C12 alkyl group or a C3-C12 cycloalkyl group, or $P^6$ and $P^7$ are bonded together to form a C3-C12 divalent acyclic hydrocarbon group which forms a ring together with the adjacent $S^+$, and at least one —$CH_2$— in the divalent acyclic hydrocarbon group may be replaced with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded together to form a divalent acyclic hydrocarbon group which forms a 2-oxocycloalkyl group together with the adjacent —CHCO—, and at least one —$CH_2$— in the divalent acyclic hydrocarbon group may be replaced with —CO—, —O— or —S—, and a cation represented by the formula (IId):

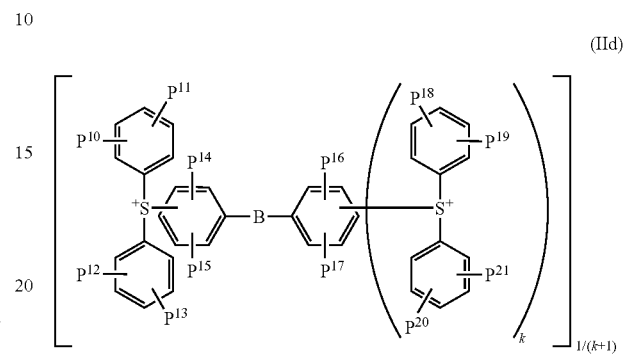
(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1.

2. A sulfonium compound represented by the formula (I):

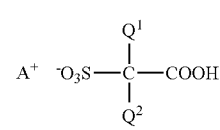
(I)

wherein $Q^1$ and $Q^2$ each independently represent a fluorine atom or a C1-C6 perfluoroalkyl group, and $A^+$ represents an organic counter ion;

wherein the organic counter ion is a cation represented by the formula (IIIa), (IIIb) or (IIIc):

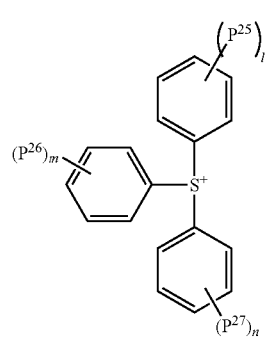
(IIIa)

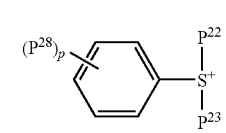
(IIIb)

-continued

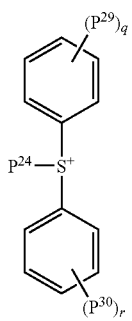
(IIIc)

wherein $P^{22}$, $P^{23}$ and $P^{24}$ each independently represent a C1-C20 alkyl group or a C3-C30 cyclic hydrocarbon group except a phenyl group, wherein at least one hydrogen atom in the C1-C20 alkyl group may be substituted with a hydroxyl group, a C1-C12 alkoxy group or a C3-C12 cyclic hydrocarbon group and wherein at least one hydrogen atom in the C3-C30 cyclic hydrocarbon group may be substituted with a hydroxyl group, a C1-C12 alkyl group or a C1-C12 alkoxy group, and $P^{25}$, $P^{26}$, $P^{27}$, $P^{28}$, $P^{29}$ and $P^{30}$ each independently represent a hydroxyl group, a C1-$C^{12}$ alkyl group, a C1-C12 alkoxy group or a C3-C12 cyclic hydrocarbon group, and l, m, n, p, q and r each independently represent an integer of 0 to 5.

3. A sulfonium compound represented by the formula (I):

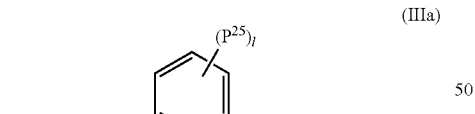
(I)

wherein $Q^1$ and $Q^2$ each independently represent a fluorine atom or a C1-C6 perfluoroalkyl group, and $A^+$ represents an organic counter ion;

wherein the organic counter ion is a cation represented by the formula (IIIa):

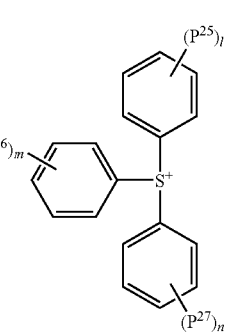
(IIIa)

wherein $P^{25}$, $P^{26}$, and $P^{27}$ each independently represent a hydroxyl group, a C1-C12 alkyl group, a C1-C12 alkoxy group, or a C3-12 cyclic hydrocarbon group, and l, m and n each independently represent an integer of 0 to 5.

4. A sulfonium compound represented by the formula (IV):

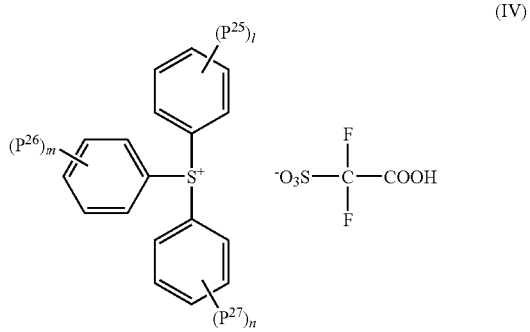
(IV)

wherein $P^{25}$, $P^{26}$, and $P^{27}$ each independently represent a hydroxyl group, a C1-C12 alkyl group, a C1-C12 alkoxy group, or a C3-C12 cyclic hydrocarbon group, and l, m and n each independently represent an integer of 0 to 5.

5. A process for production of a sulfonate compound represented by the formula (VIII):

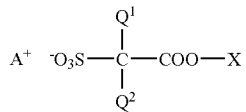
(VIII)

wherein $Q^1$ and $Q^2$ each independently represent a fluorine atom or a C1-C6 perfluoroalkyl group, $A^+$ represents an organic counter ion, and X represents a C1-C30 hydrocarbon group which may be substituted, which comprises reacting a sulfonium compound represented by the formula (I):

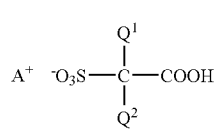
(I)

wherein $Q^1$, $Q^2$ and $A^+$ are the same as defined above, with a compound represented by the formula (VII):

HO—X (VII)

wherein X is the same as defined above.

* * * * *